United States Patent

Lang et al.

Patent Number: 5,985,253
Date of Patent: Nov. 16, 1999

[54] HAIR SHAPING COMPOSITIONS CONTAINING MERCAPTOETHYLAMINES AND METHODS FOR THE PERMANENT SHAPING OF HAIR USING SAME

[75] Inventors: Guenther Lang, Reinheim; Heiko Walther, Marburg/Lahn; Beate Dannecker, Darmstadt; Wolfgang Hanefeld, Marburg/Lahn, all of Germany

[73] Assignee: Wella AG, Darmstadt, Germany

[21] Appl. No.: 09/036,849

[22] Filed: Mar. 9, 1998

[30] Foreign Application Priority Data

Mar. 14, 1997 [DE] Germany .......................... 197 10 544

[51] Int. Cl.⁶ ................................ A61K 7/06; A61K 7/09
[52] U.S. Cl. .................... 424/70.1; 424/70.2; 424/70.51
[58] Field of Search ............................... 424/70.1, 70.2, 424/70.51

[56] References Cited

U.S. PATENT DOCUMENTS

| | | | |
|---|---|---|---|
| 3,257,361 | 6/1966 | Miskel et al. | 260/79.5 |
| 3,830,918 | 8/1974 | Molnar et al. | 424/257 |
| 3,869,554 | 3/1975 | Pittet et al. | 426/65 |
| 5,565,192 | 10/1996 | Leroy et al. | 424/70.5 |

FOREIGN PATENT DOCUMENTS

| | | | |
|---|---|---|---|
| 0 455 457 A2 | 11/1991 | European Pat. Off. | |
| 948 186 | 8/1956 | Germany | |
| 972 424 | 7/1959 | Germany | |
| 195 03 131 A1 | 8/1996 | Germany | |
| WO 91/10 421 | 7/1991 | WIPO | |

*Primary Examiner*—Thurman K. Page
*Assistant Examiner*—Lakshmi Channavajjala
*Attorney, Agent, or Firm*—Michael J. Striker

[57] ABSTRACT

The aqueous permanent shaping composition has a pH of 6.5 to 9.5 and contains water, from 3 to 28 percent by weight of one or more mercaptoethylamines of the formula I $$HS-CH_2-CH_2-NR_1R_2 \qquad (I),$$

wherein $R_1$ represents hydrogen, a straight or branched chain alkyl, hydroxyalkyl or polyhydroxyalkyl group having 1 to 6 carbon atoms; $R_2$ represents a cyclohexyl group, a furfuryl group, a straight or branched chain hydroxyalkyl group having 1 to 6 carbon atoms or a polyhydroxyalkyl group having 1 to 6 carbon atoms; or wherein $R_1$ and $R_2$ together with the nitrogen atom form a five or six membered ring containing, or not containing, another heteroatom and the five or six membered ring is substituted with a hydroxyl group, a carboxyl group or with one or two alkyl, hydroxyalkyl, polyhydroxyalkyl or alkoxycarboxyl groups having from 1 to 4 carbon atoms; or at least one physiologically compatible salt thereof; and one or more additive ingredients, which can be a surfactant or emulsifier, alcohol, sugar, solvating agent, stabilizer, buffer substance, perfume oil, dyestuff, hair conditioning or care ingredient.

11 Claims, No Drawings

HAIR SHAPING COMPOSITIONS CONTAINING MERCAPTOETHYLAMINES AND METHODS FOR THE PERMANENT SHAPING OF HAIR USING SAME

BACKGROUND OF THE INVENTION

The present invention concerns compositions for the permanent shaping of hair containing a mercaptoethylamine and/or one of its salt as keratin reducing agent and to a method for permanent shaping of hair using these compositions.

The well-known classical technique for performing a permanent shaping of hair is based on two treatment steps. In the first step the cystine-disulfide bridges of the hair keratin are opened by action of a composition (shaping composition) containing a reducing agent. Then the hair is put in the desired shape. In a second step cystine-disulfide bridges are again closed using a fixing composition, i.e. a composition containing an oxidizing agent.

Thioglycolic acid, for example as its ammonium or monoethanolamine salt, is employed as a classic permanent wave reducing agent, as shown by the German Pioneer Patents 948 186 and 972 424. Additional conventional reducing agents include inorganic sulfites, 2-mercaptopropionic acid (thiolactic acid), 3-mercaptopropionic acid, certain mercaptocarboxylic acid esters, cysteine and derivatives of these compounds.

These reducing agents however have a series of disadvantages. In spite of their sufficient action alkaline preparations based on mercaptocarboxylic acids produce hair damage, which manifests itself in multiple hair strand breaks. Many times these compositions also load the scalp skin in an undesirable manner.

Finally an intensive perfuming of the product is subsequently required because of the unpleasant smell of the reducing agent used. One can solve several of the above-mentioned problems by using 2-mercaptopropionic acid (thiolactic acid). Generally the thiolactic acid is characterized by a weaker shaping action than the generally used thioglycolic acid.

The mercaptocarboxylic acid esters, which allow hair shaping also at lower pH values, are not satisfactory in regard to their skin compatibility and their sensitization risk. Instead of the mercaptocarboxylic acid esters mercaptocarboxylic acid amides, such as thioglycolic acid amide or alkyl- and/or hydroxyalkyl-substituted amides, have also been used. These latter compounds are disclosed in International Patent Application WO-A-91/10421 and European Patent Application EP-A-0 455 457. These materials have, a comparatively good shaping power also at reduced pH values, like the carboxylic acid esters, however are still more criticized than the esters in regard to their sensitizing action. Mercaptoethylamines and their salts, in which the nitrogen atom is substituted with two equal straight or branched chain alkyl groups having from 1 to 6 carbon atoms, are already disclosed in German Patent Application 195 03 131.

SUMMARY OF THE INVENTION

It was surprisingly found that the above-described disadvantages characterizing the prior art hair shaping compositions can be avoided using the mercaptoethylamines described hereinbelow and that these compounds provide a stronger or greater shaping power than thiolactic acid.

These mercaptoethylamines have the following formula I:

$$HS-CH_2-CH_2-NR_1R_2 \quad (I),$$

wherein $R_1$ represents hydrogen, a straight or branched chain alkyl, hydroxyalkyl or polyhydroxyalkyl group having 1 to 6 carbon atoms;

wherein $R_2$ represents a straight or branched chain hydroxyalkyl or polyhydroxyalkyl group having 1 to 6 carbon atoms, cyclohexyl group or furfuryl group; or wherein $R_1$ and $R_2$ together with the nitrogen atom form a five or six membered ring, which can contain another heteroatom and can be substituted with a hydroxyl or carboxyl group or with one or two alkyl, hydroxyalkyl, polyhydroxyalkyl or alkoxycarboxyl groups having from 1 to 4 carbon atoms.

These mercaptoethylamine compounds and/or their physiologically compatible salts are used as the keratin reducing agents in the hair shaping compositions of the invention.

The mercaptoethylamines of formula I are made by reaction of a suitable amine with thiirane in toluene at 90 to 100° C. and subsequent fractional distillation.

The subject matter of the present invention comprises compositions for the permanent shaping of hair which contain at least one mercaptoethylamine of the formula I and/or at least one physiologically compatible salts thereof as the keratin reducing agent.

Compositions for the permanent shaping of hair are particularly preferred which contain a mercaptoethylamine of the formula II or III:

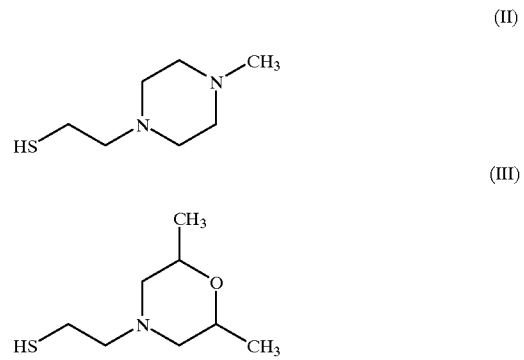

The mercaptoethylamines are used in amounts of from 3 to 28 percent by weight, preferably from 5 to 21 percent by weight, in the compositions for permanent shaping of hair. They can also be employed in a mixture with other known thiols, such as thioglycolic acid, thiolactic acid, cysteine, cysteamine and alkyl or acylcysteamine or sulfites.

The ready-to-use hair shaping composition preferably has a pH of from 6.5 to 9.5, especially preferably from 6.5 to 8.5. Ammonia or soda lye solution can be used for adjustment of the pH, however water-soluble, physiologically compatible salts of organic and inorganic bases, such as ammonium hydrogen carbonate can also be used.

The shaping composition can be provided both as a one-component and a two-component product, in which the composition can be present in the form of an aqueous solution or an emulsion and also in thickened form on an aqueous basis, especially as a cream, gel, foam or paste.

Understandably the hair shaping composition can include all those standard cosmetic additives conventionally used in this type of composition, for example thickeners, such as bentonite, fatty acids, starches, polyacrylic acids and their derivatives, cellulose derivatives, alginates, petrolatum (Vaseline®), paraffin oils; wetting agents or emulsifiers, taken from the classes of the anionic, cationic, amphoteric or nonionic surfactants, for example fatty alcohol sulfates, fatty alcohol ether sulfates, alkylsulfonates, alkylbenzene sulfates, quaternary ammonium salts, alkylbetaine, ethoxylated alkylphenols, fatty acid alkanol amides or ethoxylated fatty acid esters; turbidity-inducing agents, such as polyethyleneglycol esters; alcohols, such as ethanol, propanol, isopropanol and glycerol; sugars, such as D-glucose; solvating agents, stabilizers, buffer substances, perfume oils, dyestuffs and hair conditioning and hair care ingredients, such as cationic polymers, lanolin derivatives, cholesterol, pantothenic acids and betaine.

The above-mentioned cosmetic additives are used in standard amounts appropriate for their purposes, for example the wetting agents and emulsifiers can be contained in the hair shaping composition of the invention in concentrations of from 0.2 to 30 percent by weight, the alcohols, in an amount of from 0.1 to 20 percent by weight, the turbidity-inducing agents, perfumes and dyestuffs in an amount of 0.01 to 1 percent by weight for each, the buffer substances, in an amount of from 0.1 to 10 percent by weight; the sugars, stabilizers and hair conditioning and hair care ingredients, in an amount of from 0.1 to 5 percent by weight for each, while the thickeners and solvating agents, are each contained in an amount of from 0.5 to 20 percent by weight in the composition according to the invention.

Furthermore the hair shaping composition according to the invention can also contain ingredients which increase its effectiveness, for example the so-called swelling and penetrating agents, such as dipropyleneglycolmonomethyl ether, 2-pyrrolidone or imidazolidin-2-one, in amounts of from 1 to 30 percent by weight or dithiocompounds for preventing over-curling of the hair, such as dithioglycolic acid, dithiolactic acid, disulfides of the named compounds or their respective salts.

By changing the pH a composition which is universally suitable for each hair type can be provided, if necessary with application of additional heat. The composition for hair shaping according to the invention provides an elastic, permanent and uniform shaping from the hair roots to the hair tips, without allergic or sensitizing reactions.

The present invention also concerns a method for the permanent shaping of hair, in which the hair is brought into the desired shape either before or after it is treated with the hair shaping composition, rinsed with water and then oxidatively treated, rinsed with water again, and if necessary put in a waterwave and then dried. This method is distinguished by use of the above-described hair shaping composition according to the invention as the hair shaping composition in the method.

In a preferred embodiment of the method according to the invention the air is washed first with shampoo and after that rinsed with water. Subsequently the hand-towel dried hair is divided into individual strands and wound on curlers with a diameter of from 5 to 30 mm, preferably from 5 to 15 mm. Then the hair is treated with an amount of the hair shaping composition according to the invention which is sufficient for the hair shaping treatment, preferably from 60 to 120 g.

After a sufficient acting time for the permanent shaping of hair, which amounts to from 5 to 30 minutes (10 to 30 minutes without heating; 5 to 20 minutes with heating) according to the hair condition, the pH, the shaping effectiveness of the shaping agent and the application temperature, the hair is rinsed with water and oxidatively after-treated ("fixed"). The after-treatment composition is applied in an amount according to the hair abundance, preferably in an amount of from 80 to 100 g.

Any oxidative after-treatment composition which is suitable for this type of after-treatment can be used as the oxidative after-treatment composition on hair that is curled on curlers or not on curlers. For example, oxidizing agents suitable for use in this type of after-treatment composition include potassium bromate, sodium bromate, sodium perborate, urea peroxide and hydrogen peroxide. The concentration of the oxidizing agent different depending on the application time (usually 5 to 15 minutes) and the application temperature. Normally the oxidizing agent is present in the ready-to-use aqueous after-treatment composition in a concentration of from 0.5 to 10 percent by weight. The composition for oxidative after-treatment can understandably include additive ingredients, for example wetting agents, care ingredients such as cationic polymers, weak acids, buffer substances or peroxide stabilizers and can be in the form of an aqueous solution, an emulsion and in thickened form on an aqueous basis, especially creams, gels or pastes. The additive ingredients can be present in the after-treatment composition, particularly in an amount of from 0.1 to 10 percent by weight.

Subsequently the curlers are removed. If necessary, the hair is now oxidatively after-treated again after removing the curlers. Then the hair is rinsed with water, if necessary put in a waterwave and subsequently dried.

The following examples should illustrate the subject matter of the invention in greater detail, without however limiting the based concept of the invention or the claims appended hereinbelow.

EXAMPLES

Example 1

Preparation of 2,6-dimethyl-4-(2'-mercaptoethyl)-morpholine

In a 500 ml three necked flask 115.2 g (1 mol) 2,6-dimethylmorpholine in 250 ml of toluene is heated at 90° C. Then 60.12 g (1 mol) thiirane is added to the resulting reaction mixture dropwise and the reaction mixture is heated for 5 hours under reflux. The reaction mixture is concentrated in vacuum with a rotary evaporator and is fractionally distilled using a Vigreux column.

The yield amounts to 143.5 g of the named compound (82%).

Analysis:

a) $^1$H—NMR (CDCl$_3$):
 $\alpha$(ppm) = 3.99–3.64 (2x m, 2H, CH)
 2.67–2.5 (m,6H,HS—CH$_2$—<u>CH$_2$</u>—N + 2x N—CH$_2$)
 1.74 (t,2H, HS—CH$_2$—<u>CH$_2$</u>—N)
 1.21–1.1 (2x d, 6H, CH$_3$)

b) $^{13}$C—NMR (DCDI$_3$):
 $\alpha$(ppm) = 71.59 (2xCH)
 60.78 (HS—CH$_2$—<u>CH$_2$</u>—N)
 59.01 (2C-atoms, N—CH$_2$—<u>CH</u>—O)
 21.68 (HS—CH$_2$)
 19.06 (2C-atoms, CH$_3$)

c) MS (70 e.V., EI,RT):
 m/z(%) = (M$^+$) = 175(1.3),
 129(9.0),
 128(100),
 98(2.6),
 70(9.41),
 43(19.11),
 42(27.60).

d) thiotitration 95.48% e) elemental analysis: C$_9$H$_{19}$NOS  (MW: 175.26)
 Literature: C: 54.82  Found: C: 55.15
 H: 9.77  H: 9.27

-continued

| Analysis: | | |
|---|---|---|
| | N: 7.99 | N: 8.10 |
| | S: 18.29 | S: 18.01 |
| f) IR (NaCl-Plate): | 2972–2810s (CH$_2$) | |
| | 2546w (SH) | |
| g) HPLC | The HPLC gives a result of 94.23 percent surface for the compound (column: C 18 5U, 250 mm × 4.6 mm; eluent, acetonitrile: buffer [4 g KH$_2$PO$_4$ + 0.8 g octanesulfonoic acid sodium salt + 2 ml H$_3$PO$_4$] = 25:75; flow rate = 0.5 ml/min; wavelength 200 mm) | |
| h) pKs | 6.559 (H$_2$O) | |
| i) UV-max | < 200 mm (acetonitrile: buffer = 25:75) | |
| j) boiling point | 55° C./0.05 torr | |

Example 2

Preparation of 2,6-dimethyl-1-(2'-mercaptoethyl)-piperidine

In a 500 ml three-necked flask 113.2 g(1 mol) of 2,6-dimethylpiperidine in 250 mol toluene was heated at 90° C. Then 60.12 g (1 mol) thiirane is added to the resulting reaction mixture dropwise and the reaction mixture is heated for 5 hours under reflux. The reaction mixture is concentrated in vacuum with a rotary evaporator and is fractionally distilled using a Vigreux column. The yield amounts to 60.55 g of the named compound(35%).

| Analysis: | | |
|---|---|---|
| a) H—NMR (CDCl$_3$): | | |
| α(ppm) = | 2.87 | (m,2H,HS—CH$_2$—<u>CH$_2$</u>—N) |
| | 2.53 | (m,2H,HS—<u>CH$_2$</u>—CH$_2$—N) |
| | 2.49 | (m,2H,N(—<u>CH</u>—CH$_2$—)$_2$) |
| | 1.54 | (t,1H,HS) |
| | 1.53 | (m,2H,N—CH—CH$_2$—<u>CH$_2$</u>) |
| | 1.23 | (m,2H,N(—CH—<u>CH$_2$</u>—)$_2$) |
| | 1.08 | (d, 6H, CH$_3$) |
| b) $^{13}$C—NMR (DCDI$_3$): | | |
| α(ppm) = | 55.90 | (2xCH) |
| | 52.53 | (S—CH$_2$—<u>CH$_2$</u>—N) |
| | 34.62 | (2C-atoms,N—CH—<u>CH$_2$</u>) |
| | 24.55 | (HS—CH$_2$) |
| | 21.36 | (2C-atoms,CH$_3$) |
| | 20.15 | (N—CH—CH$_2$—<u>CH$_2$</u>) |
| c) MS (70 e.V., EI,60° C.): | | |
| m/z(%) = (M$^+$) = | 173(0.8), | |
| | 172(4.4), | |
| | 126(100), | |
| | 98(11.21), | |
| | 70(4.58), | |
| | 56(5.6), | |
| | 42(7.43) | |
| d) thiotitration 99.66% | | |
| e) elemental analysis: C$_9$H$_{19}$NS (MW: 173.26) | | |
| Literature: | C: 62.39 Found: | C: 62.40 |
| | H: 11.05 | H: 11.22 |
| | N: 8.09 | N: 8.00 |
| | S: 18.50 | S: 18.22 |
| f) IR (NaCl-Plate): | 2966–2788s (CH$_2$) | |
| | 2591w (SH) | |
| g) HPLC | The HPLC gives a result of 100 percent surface for the compound (column: C 18 5U, 250 mm × 4.6 mm; eluent, acetonitrile: buffer [4 g KH$_2$PO$_4$ + 0.8 g octanesulfonoic acid sodium salt + 2 ml H$_3$PO$_4$] 25:75; flow rate = 0.5 ml/min; wavelength 200 mm) | |
| h) pKs | 7.72 (H$_2$O) | |
| i) UV-max | < 200 mm (acetonitrile: buffer = 25:75) | |
| j) boiling point | 51° C./0.1 torr | |

Example 3

Comparison of Waving Effectiveness

The waving effectiveness of 2-mercaptoethylamines, measured as normalized wave stability (WSN), was determined using glycerol monothioglycolate as a comparative substance with the aid of a waving solution at pH=7, 8 and 9. A 16.5 cm length of prebleached and thus damaged hair strands (about 100 hair strands) of central European hair were wound or curled on a standard spiral curler (inner diameter: 3 mm) and after conditioning in a climate controlled room (temperature 20°C.; humidity, 65%) were treated with an 87 mmol/100 g solution of the reducing agent adjusted to the respective pH values. The applied amount of waving liquid was determined from a ratio of 1:1.2 (i.e. 1 g of the hair was treated with 1.2 ml of the waving liquid). The acting temperature amounted to 50° C. and the acting time amounted to 20 minutes. Subsequently the hair was fixed with a peroxide containing fixing agent, dried and after being unwound from the curler was suspended for four hours in water (water bath temperature: 40° C.).

The wave stability is given by the following formula IV:

$$\text{Wave stability in } \% = (l_o - l_t)/(l_o - l_1) \times 100 \qquad (IV)$$

wherein $l_o$=the total length of the untreated hair strands (16.5 cm) prior to stretching;

$l_t$=the total length of the unwound, suspended strands after 240 minutes; and $l_1$=the total length of the shaped strands wound on a curler of inner diameter 3 mm: $l_1$=i.e. 35 cm.

The strands were treated with a suitable glycerol monothioglycolate solution having a pH=9 as a standard for the comparison. The normalized wave stabilities given in the following Table 1 are the measured wave stabilities related to the wave stability of this standard solution (pH=9) whose wave stability is set at 100% (i.e. the wave stabilities in the table equal the measured wave stability for the particular entry in the Table divided by the wave stability of the standard solution times 100.).

Table 1 shows that the wave stabilities obtained by treating the hair with the compositions according to the invention including mercaptoethylamines at pH=7, 8 and 9 are significantly higher than those obtained with compositions including thiolactic acid.

TABLE I

COMPARATIVE WAVE STABILITIES (WSN) FOR TREATMENT WITH COMPOSITIONS CONTAINING THE FOLLOWING MERCAPTOETHYLAMINES

| EXPER. # | MERCAPTOETHYLAMINE | WSN pH = 7 | WSN pH = 8 | WSN pH = 9 |
|---|---|---|---|---|
| 1 | 2,6-dimethyl-4-(2'-mercaptoethyl)-morpholine from 2,6-Dimethylmorpholine | 63 | 63 | 68 |

TABLE I-continued

COMPARATIVE WAVE STABILITIES (WSN) FOR TREATMENT WITH
COMPOSITIONS CONTAINING THE FOLLOWING MERCAPTOETHYLAMINES

| EXPER. # | MERCAPTOETHYLAMINE | WSN pH = 7 | WSN pH = 8 | WSN pH = 9 |
|---|---|---|---|---|
| 2 | 2,6-dimethyl-1-(2'-mercaptoethyl)-piperidine from 2,6-Dimethylpiperidine | 61 | 74 | 71 |
| 3 | N-cyclohexyl-N-2-mercaptoethylamine from cyclohexylamine | 77 | 83 | 86 |
| 4 | N-(4-methyl-1-piperazinyl)-mercapto-ethylamine from N-methylpiperazine | 70 | 91 | 93 |
| 5 | N-(2'-mercaptoethyl)-piperidin-4-carboxylic-acid ethyl ester from piperidine 4-carboxylic acid ethyl ester | 74 | 65 | 59 |
| 6 | 2-(2-furanylmethyl)aminomercapto-ethylamine from furfurylamine | 85 | 80 | 87 |
| 7 | 2-ethyl-N-(2'-mercaptoethyl)piperidine from 2-ethylpiperidine | 74 | 75 | 77 |
| 8 | N-(2-mercaptoethyl)ethylamino-2-hydroxy-ethanol from ethylhydroxyethylamine | 74 | 82 | 96 |
| 9 | N-(2'-mercaptoethyl)morpholine from morpholine | 60 | 93 | 95 |
| 10 | N-(2'-mercaptoethyl)pyrrolidine from pyrrolidine | 85 | 96 | 97 |
| 11 | N-(2'-mercaptoethyl)piperidine from piperidine | 83 | 91 | 92 |
| | thiolactic acid for comparison | 57 | 50 | 70 |

Example 4
Permanent Wave Shaping Composition for Dyed Hair

```
9.76 g   N-(2'-mercaptoethyl)piperidin-4-carboxyl acid
         ethyl ester
0.40 g   ammonia (25% aqueous solution) to set pH
2.00 g   ammonium hydrogen carbonate
2.00 g   isopropanol
1.00 g   isooctylphenol, ethoxylated with 10 mol
         ethylene oxide
1.00 g   poly(dimethyldiallylammonium chloride)
0.30 g   perfume oil
0.10 g   vinylpyrrolidone/styrene mixed polymerizate
         (Antara ® 430 of GAF Corp, New York, U.S.A.)
83.44 g  water
─────────
100.00 g
```

The pH of this composition amounts to from 7.0 to 7.5.

Hair damaged by dyeing is washed with a shampoo, rubbed with a hand towel and wound on curlers with a diameter of 8 mm. Subsequently the above-described hair shaping composition is distributed uniformly on the hair. Then the hair is covered with a plastic hood and heated for 10 minutes under a drying hood at a temperature of 45° C. Subsequently the covering is removed, the hair is rinsed with water and oxidatively after-treated with 100 g of a 3% aqueous hydrogen peroxide solution. After removal from the curlers the hair is rinsed again with water, put in a water-wave and subsequently dried. The hair so treated has a uniform, resilient and permanent shaping.

Example 5
Permanent Wave shaping Composition for Normal Hair

```
16.95 g  2,6-dimethyl-1-(2'-mercaptoethyl)piperidine
8.90 g   ammonia (25% aqueous solution)
5.00 g   ammonium hydrogen carbonate
4.00 g   urea
2.40 g   monoethanolamine
1.50 g   isooctylphenol, ethoxylated with 10 mol
         ethylene oxide
0.50 g   poly(dimethyldiallylammonium chloride)
0.50 g   perfume oil
0.10 g   vinylpyrrolidone/styrene mixed polymerizate
         (Antara ® 430 of GAF corp, New York, U.S.A.)
60.15 g  water
─────────
100.00 g
```

The pH of this composition amounts to from 8.0 to 8.5.

Normal, undamaged hair is washed, rubbed with a hand towel and wound on curlers with a diameter of 6 mm. Subsequently the hair is thoroughly and uniformly moistened with the above-described hair shaping composition. After an acting time of 15 minutes the hair is rinsed with water and then is oxidatively after-treated with 80 g of a 3% aqueous hydrogen peroxide solution. After removal from the curlers the hair is rinsed again with water, put in a water-wave and subsequently dried. The hair so treated has a uniform and lively curl.

Example 6
Permanent Wave Shaping Composition for Normal Hair

```
6.42 g   N-(2'-mercaptoethyl) pyrrolidine
4.51 g   thioglycolic acid
8.90 g   ammonia (25% aqueous solution) to set pH
5.00 g   ammonium hydrogen carbonate
4.00 g   urea
2.40 g   monoethanolamine
1.50 g   isooctylphenol, ethoxylated with 10 mol
         ethylene oxide
0.50 g   poly(dimethyldiallylammonium chloride)
0.50 g   perfume oil
0.10 g   vinylpyrrolidone/styrene mixed polymerizate
         (Antara ® 430 of GAF corp, New York, U.S.A.)
66.17 g  water
─────────
100.00 g
```

The pH of this composition amounts to from 8.0 to 8.5.

Normal, undamaged hair is washed, rubbed with a hand towel and wound on curlers with a diameter of 6 mm. Subsequently the hair is thoroughly and uniformly moistened with the above-described hair shaping composition. After an acting time of 15 to 25 minutes the hair is rinsed with water and then is oxidatively after-treated with 80 g of a 3% aqueous hydrogen peroxide solution. After removal from the curlers the hair is rinsed again with water, put in a waterwave and subsequently dried. The hair so treated has a uniform and lively curl.

The disclosure in German Patent Application 197 10 544.0 of Mar. 14, 1997 is incorporated here by reference. This German Patent Application, describes the invention described hereinabove and claimed in the claims appended hereinbelow and provides the basis for a claim of priority for the instant invention under 35 U.S.C. 119. While the invention has been illustrated and described as embodied in hair shaping compositions containing mercaptoethylamines and methods for the permanent shaping of hair using same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. An aqueous composition for permanent shaping of hair, said composition having a pH of from 6.5 to 9.5 and comprising:

from 3 to 28 percent by weight of at least one mercaptoethylarnine of the formula I as keratin reducing agent:

$$HS\text{—}CH_2\text{—}CH_2\text{—}NR_1R_2 \quad (I),$$

wherein $R_1$ represents hydrogen, a straight or branched chain alkyl, hydroxyalkyl or polyhydroxyalkyl group having 1 to 6 carbon atoms; $R_2$ represents a cyclohexyl group, a furfuryl group, a straight or branched chain hydroxyalkyl group having 1 to 6 carbon atoms or a polyhydroxyalkyl group having 1 to 6 carbon atoms; or wherein $R_1$ and $R_2$ together with the nitrogen atom form a six membered ring containing or not containing another heteroatom and said six membered ring is substituted with a hydroxyl group, a carboxyl group or with one or two alkyl, hydroxyalkyl, polyhydroxyalkyl or alkoxycarboxyl groups having from 1 to 4 carbon atoms; or wherein $_1$ and $R_2$ together with the nitrogen atom form a five membered ring containing or not containing another heteroatom and said five membered ring is substituted with a hydroxyl group, a carboxy group or with one or two hydroxyalkyl, polyhydroxyalkyl or alkoxycarboxyl groups having from 1 to 4 carbon atoms; or at least one physiologically compatible salt thereof;

water; and at least one cosmetic additive ingredient selected from the group consisting of thickeners, anionic surfactants, cationic surfactants, amphoteric surfactants, nonionic surfactants, turbidity-inducing agents, alcohols, sugars, solvating agents, stabilizers, buffer substances, perfume oils, dyestuffs, hair conditioning materials and hair care ingredients;

wherein, if present in said composition, said surfactants are present in a concentration of from 0.2 to 30 percent by weight; said alcohols, in a concentration of from 0.1 to 20 percent by weight; said turbidity-inducing agents, said perfume oils and said dye stuffs, each in a concentration of from 0.01 to 1 percent by weight; said buffer substances, in an amount of from 0.1 to 10 percent by weight; said sugars, stabilizers, hair conditioning and hair care ingredients, each in an amount of from 0.1 to 5 percent by weight; and said thickeners and said solvating agents, each in an amount of from 0.5 to 20 percent by weight.

2. The composition as defined in claim 1, wherein said at least one mercaptoethylamine is a compound of the formula II or III:

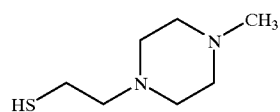

(II)

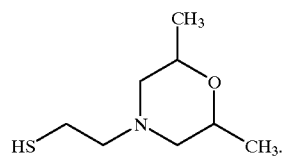

(III)

3. A method for permanent shaping of hair, said method comprising the steps of:

a) treating the hair with an aqueous composition for permanent shaping of hair;

b) before or after the treating of step a) putting the hair in a predetermined shape;

c) rinsing the hair with water after steps a) and b);

d) performing an oxidative-after treatment of the hair;

e) after performing the oxidative-after treatment of step d) rinsing the hair again with water; and f) putting the hair in a waterwave, if necessary, and then drying the hair;

wherein said composition for permanent shaping of hair has a pH of 6.5 to 9.5 and contains from 3 to 28 percent by weight of at least one mercaptoethylamine of the formula I as keratin reducing agent:

$$HS\text{—}CH_2\text{—}CH_2\text{—}NR_1R_2 \quad (I),$$

wherein $R_1$ represents hydrogen, a straight or branched chain alkyl, hydroxyalkyl or polyhydroxyalkyl group having 1 to 6 carbon atoms; $R_2$ represents a cyclohexyl group, a furfuryl group, a straight or branched chain hydroxyalkyl group having 1 to 6 carbon atoms or a polyhydroxyalkyl group having 1 to 6 carbon atoms; or wherein $R_1$ and $R_2$ together with the nitrogen atom form a five or six membered ring containing or not containing another heteroatom and said five or six membered ring is substituted with a hydroxyl group, a carboxyl group or with one or two alkyl, hydroxyalkyl, polyhydroxyalkyl or alkoxycarboxyl groups having from 1 to 4 carbon atoms; or at least one physiologically compatible salt thereof;

water; and at least one cosmetic additive ingredient selected from the group consisting of thickeners, anionic surfactants, cationic surfactants, amphoteric surfactants, nonionic surfactants, turbidity-inducing agents, alcohols, sugars, solvating agents, stabilizers, buffer substances, perfume oils, dyestuffs, hair conditioning materials and hair care ingredients.

4. The method as defined in claim 3, wherein said treating with said composition for the permanent shaping of the hair includes allowing said composition to act on the hair for from 5 to 30 minutes.

5. The method as defined in claim 4, wherein said composition acts on the hair for from 5 to 20 minutes, and further comprising heating the hair.

6. The method as defined in claim 3, wherein said treating includes applying from 60 to 120 g of said composition to the hair.

7. An aqueous composition for permanent shaping of hair, said composition having a pH of from 6.5 to 9.5 and comprising:

from 3 to 28 percent by weight of at least one mercaptoethylamine of the formula II or III as keratin reducing agent;

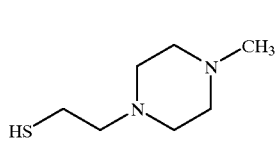

(II)

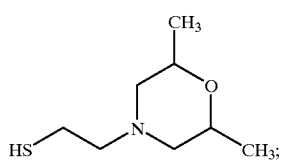

(III)

water; and
at least one cosmetic additive ingredient selected from the group consisting of thickeners, anionic surfactants, cationic surfactants, amphoteric surfactants, nonionic surfactants, turbidity-inducing agents, alcohols, sugars, solvating agents, stabilizers, buffer substances, perfume oils, dyestuffs, hair conditioning materials and hair care ingredients;
wherein, if present in said composition, said surfactants are present in a concentration or from 0.2 to 30 percent by weight; said alcohols, in a concentration of from 0.1 to 20 percent by weight; said turbidity-inducing agents, said perfume oils and said dye stuffs, each in a concentration of from 0.01 to 1 percent by weight; said buffer substances, in an amount of from 0.1 to 10 percent by weight; said sugars, stabilizers, hair conditioning and hair care ingredients, each in an amount of from 0.1 to 5 percent by weight; and said thickeners and said solvating agents, each in an amount of from 0.5 to 20 percent by weight.

8. A method for permanent shaping of hair, said method comprising the steps of:
a) treating the hair with an aqueous composition for permanent shaping of hair;
b) before or after the treating of step a) putting the hair in a predetermined shape;
c) rinsing the hair with water after steps a) and b);
d) performing an oxidative-after treatment of the hair;
e) after performing the oxidative-after treatment of step d) rinsing the hair again with water; and
f) putting the hair in a waterwave, if necessary, and then drying the hair;
wherein said aqueous composition for permanent shaping of hair has a pH of 6.5 to 9.5 and contains from 3 to 28 percent by weight of at least one mercaptoethylamine of the formula II or III as keratin reducing agent:

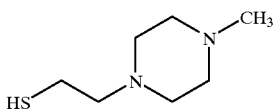

(II)

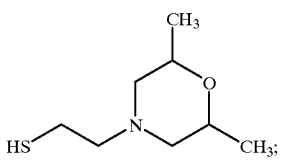

(III)

water; and
at least one cosmetic additive ingredient selected from the group consisting of thickeners, anionic surfactants, cationic surfactants, amphoteric surfactants, nonionic surfactants, turbidity-inducing agents, alcohols, sugars, solvating agents, stabilizers, buffer substances, perfume oils, dyestuffs, hair conditioning materials and hair care ingredients.

9. The method as defined in claim 8, wherein said treating with said aqueous composition for the permanent shaping of the hair includes allowing said aqueous composition to act on the hair for from 5 to 30 minutes.

10. The method as defined in claim 9, wherein said aqueous composition acts on said hair for from 5 to 20 minutes, and further comprising heating the hair.

11. The method as defined in claim 8, wherein said treating includes applying from 60 to 120 g of said aqueous composition to the hair.

* * * * *